(12) United States Patent
Righter

(10) Patent No.: US 11,506,620 B1
(45) Date of Patent: Nov. 22, 2022

(54) CONTROL OF OXYGEN FUGACITY IN A HIGH PRESSURE SOLID MEDIA ASSEMBLY USING A DOUBLE CAPSULE

(71) Applicant: United States of America as represented by the Administrator of the National Aeronautics and Space Administration, Washington, DC (US)

(72) Inventor: Kevin Righter, Houston, TX (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 125 days.

(21) Appl. No.: 16/513,087

(22) Filed: Jul. 16, 2019

Related U.S. Application Data

(60) Provisional application No. 62/701,066, filed on Jul. 20, 2018.

(51) Int. Cl.
| | |
|---|---|
| *G01N 25/00* | (2006.01) |
| *G01N 23/203* | (2006.01) |
| *C01G 41/00* | (2006.01) |
| *C01F 7/162* | (2022.01) |
| *C01G 37/14* | (2006.01) |

(52) U.S. Cl.
CPC ............. *G01N 25/00* (2013.01); *C01F 7/162* (2013.01); *C01G 37/14* (2013.01); *C01G 41/006* (2013.01); *G01N 23/203* (2013.01); *C01P 2002/32* (2013.01)

(58) Field of Classification Search
None
See application file for complete search history.

(56) References Cited

U.S. PATENT DOCUMENTS

| | | | |
|---|---|---|---|
| 3,576,730 A | 4/1971 | Spacil | |
| 4,115,230 A | 9/1978 | Beckman | |
| 4,399,022 A | 8/1983 | Nakajima et al. | |
| 5,344,549 A | 9/1994 | Dees | |
| 5,580,439 A | 12/1996 | Baucke et al. | |
| 5,596,134 A | 1/1997 | Phillippi et al. | |
| 6,340,418 B1 | 1/2002 | Turkdogan | |

(Continued)

FOREIGN PATENT DOCUMENTS

| | | |
|---|---|---|
| CN | 202962410 U | 6/2013 |
| CN | 204903454 U | 12/2015 |
| CN | 205786559 U | 12/2016 |
| CN | 107561241 A | 1/2018 |
| CN | 107736959 A | 3/2018 |
| EP | 0245717 A2 | 11/1987 |

(Continued)

OTHER PUBLICATIONS

Over "Oxygen fugacity, temperature reproducibility, and H2O contents of nominally anhydrous piston-cylinder experiments using graphite capsules", 2008, E. Medard, C. A. McCammon, J. A. Barr, T. L. Grove, 10.2138/am.2008.2842, American Mineralogist (Year: 2008).*

Shao, Tongbin & Xia, Ying & Ding, Xing & Cai, Yongfeng & Song, Maoshuang. (2018). Zircon saturation in terrestrial basaltic melts and its geological implications. Solid Earth Sciences. 4. 10.1016/j.sesci.2018.08.001. (Year: 2018).*

(Continued)

*Primary Examiner* — Erica S Lin
(74) *Attorney, Agent, or Firm* — Kurt G. Hammerle; Edward K. Fein

(57) ABSTRACT

A double capsule assembly includes an outer capsule and an inner capsule configured to be positioned within the outer capsule. The inner capsule is configured to have a sample positioned therein. The double capsule assembly is configured to be placed in a solid media assembly to analyze or synthesize the sample.

12 Claims, 7 Drawing Sheets

(56) References Cited

U.S. PATENT DOCUMENTS

2013/0296603 A1* 11/2013 Huang ............... C07C 67/00
560/239
2014/0151604 A1* 6/2014 Gullikson ............... G01L 11/00
252/408.1

FOREIGN PATENT DOCUMENTS

| WO | WO2010117304 A1 | 10/2010 |
|---|---|---|
| WO | WO 2017096711 A1 | 6/2017 |

OTHER PUBLICATIONS

Mendybaev, et al. Measurement of oxygen fugacties under reducing conditions: Non-Nemstian behavior of Y2O3-doped zirconia oxygen sensors, Geochimica et Cosmachimica Acta (1998) 62(18) 3131-3139 doi:10.1016/S0016-7037(98)00212-9 http://pdfs.semanticscholar.org/7d11/ac8d8891bddec17a5612b889a686bcd949f7.9df.

Jakobsson, "Oxygen fugacity control in piston-cylinder experiments," Contributions to Mineralogy and Petrology (Sep. 2012) 164(3)397-406: doi.10.1007/s00410-012-0743-7 https://link.springer.com/article/10.1007/s00410-012-0743-7.

Boujibar, A., et al, "Metal-silicate partitioning of sulphur, new experimental and hermodynamic constraints on planetary accrstion," Earth and Planetary Science Letters 2014) 391-42-59; doll: 10.1016/j.epsi.2014.01 021 https://www.aciencedirect.com/science/article/piiS0012821X1_4000314.

* cited by examiner

CONTROL OF OXYGEN FUGACITY IN A HIGH PRESSURE SOLID MEDIA ASSEMBLY USING A DOUBLE CAPSULE

CROSS-REFERENCE TO RELATED APPLICATIONS

This application claims priority to U.S. Provisional Patent Application No. 62/701,066, filed on Jul. 20, 2018, the entirety of which is incorporated by reference herein.

ORIGIN OF THE INVENTION

The invention described herein was made by employee(s) of the United States Government and may be manufactured and used by or for the Government of the United States of America for governmental purposes without the payment of any royalties thereon or therefor.

BACKGROUND

A solid media assembly may be used to heat a sample in a solid ceramic or salt pressure medium. More particularly, the sample in the medium may be heated and pressurized in a furnace of the solid media assembly. It may be difficult to control the oxygen fugacity in the solid media assembly due to the high temperature and/or high pressure because the conventional components of the solid media assembly are made of materials that do not control oxygen fugacity.

SUMMARY

A double capsule assembly is disclosed. The double capsule assembly includes an outer capsule and an inner capsule configured to be positioned within the outer capsule. The inner capsule is configured to have a sample positioned therein. The double capsule assembly is configured to be placed in a solid media assembly to analyze or synthesize the sample.

A solid media assembly is also disclosed. The solid media assembly includes a furnace and a double capsule assembly positioned within the furnace. The double capsule assembly includes an outer capsule, an inner capsule configured to be positioned within the outer capsule, and a layer positioned between the outer capsule and the inner capsule. The inner capsule is configured to have a sample positioned therein.

A method for analyzing or modifying a sample is also disclosed. The method includes placing a sample in an inner capsule. The method also includes placing the inner capsule in an outer capsule, thereby producing a double capsule assembly. The method also includes placing the double capsule assembly in a solid media assembly. The method also includes increasing a temperature of the sample in the solid media assembly.

A method for controlling oxygen fugacity in a solid media assembly is also disclosed. The method includes providing a double capsule having an outer capsule and an inner capsule for surrounding a sample of interest. The method also includes making at least a portion of the outer capsule from a refractory metal. The inner capsule includes a different material than the refractory metal of the outer capsule. The method also includes positioning a metal-oxide powder of the same corresponding refractory metal between an inner surface of the outer capsule and an outer surface of the inner capsule to form an oxygen buffer layer once operation of the solid media assembly begins.

Other aspects and features of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the presently described subject matter and should not be used to limit it. The present subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 6A shows the results where the outer capsule is made from or includes molybdenum (Mo). A thin layer of molybdenum oxide ($MoO_2$) is positioned at the bottom of the outer capsule. The inner capsule is made from or includes magnesium oxide (MgO). FIG. 6B shows results where the outer capsule is made from or includes chromium (Cr). A thin layer of a chromium trioxide ($Cr_2O_3$) is positioned on the left inside edge of the outer capsule. The inner capsule is made from or includes magnesium oxide (MgO), spinel ($MgAl_2O_4$), and vanadium oxide ($V_2O_3$). FIG. 6C shows the results where the outer capsule is made from or includes tungsten (W). A thin layer of magnesium tungsten oxide ($MgWO_4$) is positioned at the bottom of the outer capsule. The inner capsule is made from or includes magnesium oxide (MgO).

DETAILED DESCRIPTION

Introduction

Oxygen fugacity, also denoted in shorthand as "$fO_2$" herein, is an intensive parameter that controls fundamental chemical and physical properties in planetary materials. In terrestrial magmas, high $fO_2$ promotes magnetite stability, and low $fO_2$ causes Fe-enrichment due to magnetite suppression. In lunar and asteroidal basalts, low $fO_2$ can allow Fe metal to be stable.

Experimental studies and material synthesis may be more useful if they are performed at a specific and relevant $fO_2$ for the sample of interest. Control of oxygen fugacity in a solid media assembly or apparatus (e.g., a piston-cylinder assembly or a multi-anvil press assembly) may depend upon on either sliding sensors or graphite capsule buffering. Both of these approaches are of limited application to the wide range of oxygen fugacity recorded in planetary or extraterrestrial materials. Described in further detail below is an example of a double capsule assembly that allows oxygen fugacity to be specified and controlled across a wide range of values relevant to the study of natural samples and to the synthesis of new materials.

In one embodiment described herein, a solid media assembly (e.g., a piston-cylinder assembly or a multi-anvil press assembly) may include a double capsule assembly for controlling oxygen fugacity. The double capsule assembly may include two capsules in a layered arrangement. More particularly, a first (e.g., outer) capsule may be made from or include a refractory metal in combination with a (e.g., thin) layer of the same corresponding metal but in a metal-oxide powder form. The outer capsule may at least partially surround a second (e.g., inner) capsule. The inner capsule may be made from or include a different material than the outer capsule, such as graphite or a metal oxide compound (e.g., alumina ($Al_2O_3$) or magnesium oxide (MgO)).

During use of the solid media assembly, a sample material of interest for study or synthesis is placed inside the inner capsule. Use of the double capsule disclosed herein enables control of oxygen fugacity ($fO_2$) at high pressure and/or high temperature conditions for small volume furnaces, providing a large range of study and synthesis of materials.

Double Capsule Assembly

Systems and methods described herein are related to making and using a double capsule assembly as a component of a solid media assembly containing a sample or material of interest. The double capsule assembly may be inserted into and/or positioned within the solid media assembly. In one embodiment, the double capsule assembly may be or include a piston-cylinder assembly with a three-dimensional geometry. However, the double capsule assembly may also or instead include other three-dimensional geometrical shapes as a container for the sample or material of interest, such as a cube, a rectangular prism or cuboid, a sphere, etc.

Figure 1:
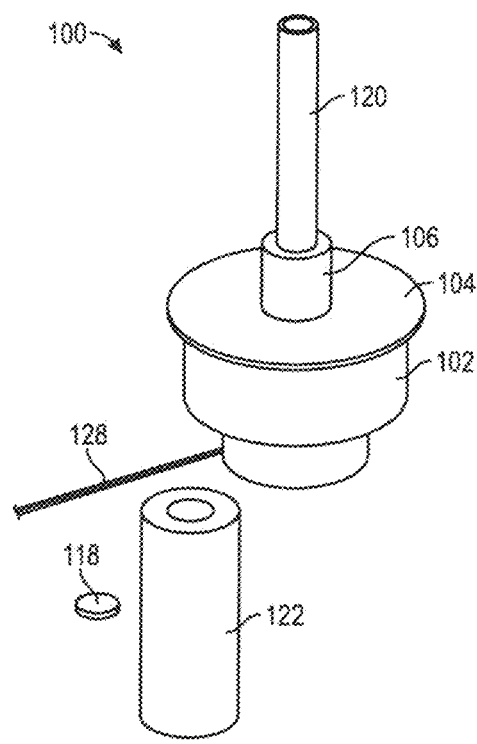
FIG. 1 shows a perspective view of a solid media assembly (e.g., a piston-cylinder assembly), according to an embodiment.
Figure 2:
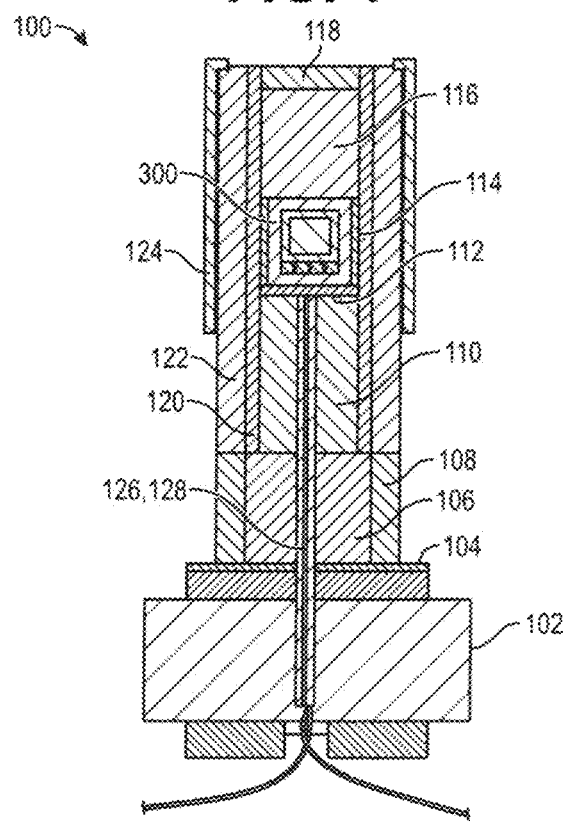
FIG. 2 shows a schematic, cross-sectional view of the solid media assembly from FIG. 1 including a double capsule assembly, according to an embodiment.

FIG. 1 shows a perspective view of a partially disassembled solid media assembly 100, and FIG. 2 shows a schematic, cross-sectional view of the assembled solid media assembly 100 including a double capsule assembly 3M), according to an embodiment. In the embodiment shown in FIGS. 1 and 2, the solid media assembly 100 is a piston-cylinder assembly (as compared to the multi-anvil press assembly shown in FIG. 4A).

The solid media assembly 100 may include a base support block 102. An insulating material (e.g., paper) 104 may be positioned on the base support block 102. A base plug 106 may be positioned on and/or above the insulating material 104. A sleeve 108 may be positioned on and/or above the insulating material 104 and/or around the base plug 106. The sleeve 108 may be made from, for example, PYREX®. A bushing 110 may be positioned on and/or above the base plug 106. The bushing 110 may be made from a material that is configured to be crushed or deformed during the method disclosed below, such as magnesium oxide (MgO). A disk 112 may be positioned on and/or above the bushing 110. The disk 112 may be made from, for example, alumina.

The double capsule assembly 300 (shown in FIG. 2) may be positioned on and/or above the disk 112. The double capsule assembly 300 is described in greater detail with respect to FIG. 3 below. A powder 114 may be positioned on and/or above the disk 112 and/or at least partially around the double capsule assembly 300. The powder 114 may be or include aluminum oxide ($Al_2O_3$). A rod 116 may be positioned on and/or above the double capsule assembly 300 and/or the powder 114. The rod 116 may be made from a material that is configured to be crushed or deformed during the method disclosed below, such as magnesium oxide (MgO). A cap 118 may be positioned on and/or above the rod 116. The cap 118 may be made from, for example, graphite.

A furnace 120 may be positioned on and/or above the base plug 106. The furnace 120 may also be positioned at least partially around the bushing 110, the disk 112, the double capsule assembly 300, the rod 116, the cap 118, or a combination thereof. The furnace 120 may be made of, for example, graphite. The furnace 120 may be configured to heat the enclosed sample at an elevated pressure. A cell 122 may be positioned on and/or above the sleeve 108. The cell 122 may be positioned around the furnace 120 and configured to generate static pressure under compression. In at least one embodiment, a foil 124 made of, for example, lead (Pb) may be positioned at least partially around the cell 120 to help reduce friction in the solid media assembly 100.

The base support block 102, insulating material 104, base plug 106, and/or bushing 110 may define a bore 126 through which one or more wires 128 may extend. The wires 128 may be or include TC wires with TEFLON® tubing. The wires 128 may be connected beneath the disk 112 and/or the double capsule assembly 300 and configured to measure temperature in the solid media assembly 100.

Figure 3:
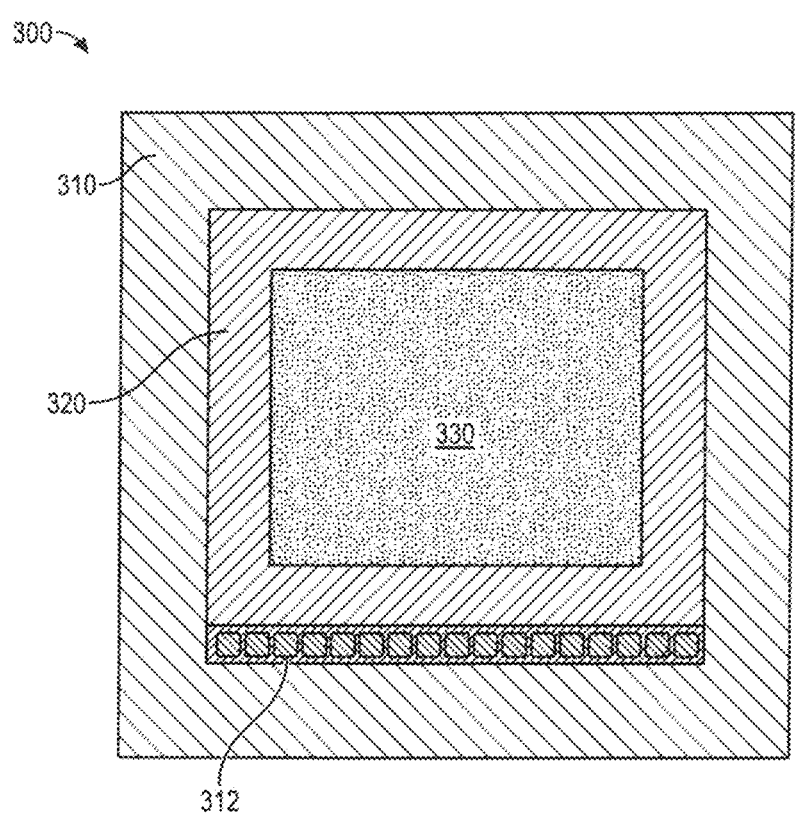
FIG. 3 shows a schematic, cross-sectional view of the double capsule assembly from FIGS. 1 and 2, according to an embodiment.

FIG. 3 shows a schematic, cross-sectional view of the double capsule assembly 300, according to an embodiment. The double capsule assembly 300 may be positioned within the solid media assembly 100 (e.g., in the piston-cylinder embodiment shown in FIGS. 1 and 2 or in the multi-anvil embodiment shown in FIGS. 4A and 4B). The double capsule assembly 300 may include a first (e.g., outer) capsule 310 and a second (e.g., inner) capsule 320.

The outer capsule 310 may be made of a layer of refractory metal such as iron (Fe), nickel (Ni), cobalt (Co), molybdenum (Mo), tungsten (W), vanadium (V), chromium (Cr), or niobium (Nb). In at least one embodiment, the double capsule assembly 300 and/or the outer capsule 310 may include a layer of a corresponding metal oxide powder 312 of the same refractory metal such as iron oxide (FeO), nickel oxide (NiO), cobalt oxide (CoO), molybdenum oxide ($MoO_2$), tungsten oxide ($WO_2$), vanadium oxide ($V_2O_3$), chromium oxide ($Cr_2O_3$), or niobium oxide ($Nb_2O_5$). For example, the layer 312 may be positioned between an inner surface of the outer capsule 310 and an outer surface of the inner capsule 320. The layer 312 may have a thickness from about 100 µm to about 200 µm.

The combination of the refractory metal (i.e., the outer capsule 310) and the metal oxide powder (e.g., the layer 312) may form an oxygen buffer as it surrounds the inner capsule 320. The refractory metal and metal oxide powder (i.e., the buffer) may react, equilibrate, and/or establish the oxygen pressure in the outer and inner capsules 310, 320 of the double capsule assembly 300.

Figure 7:
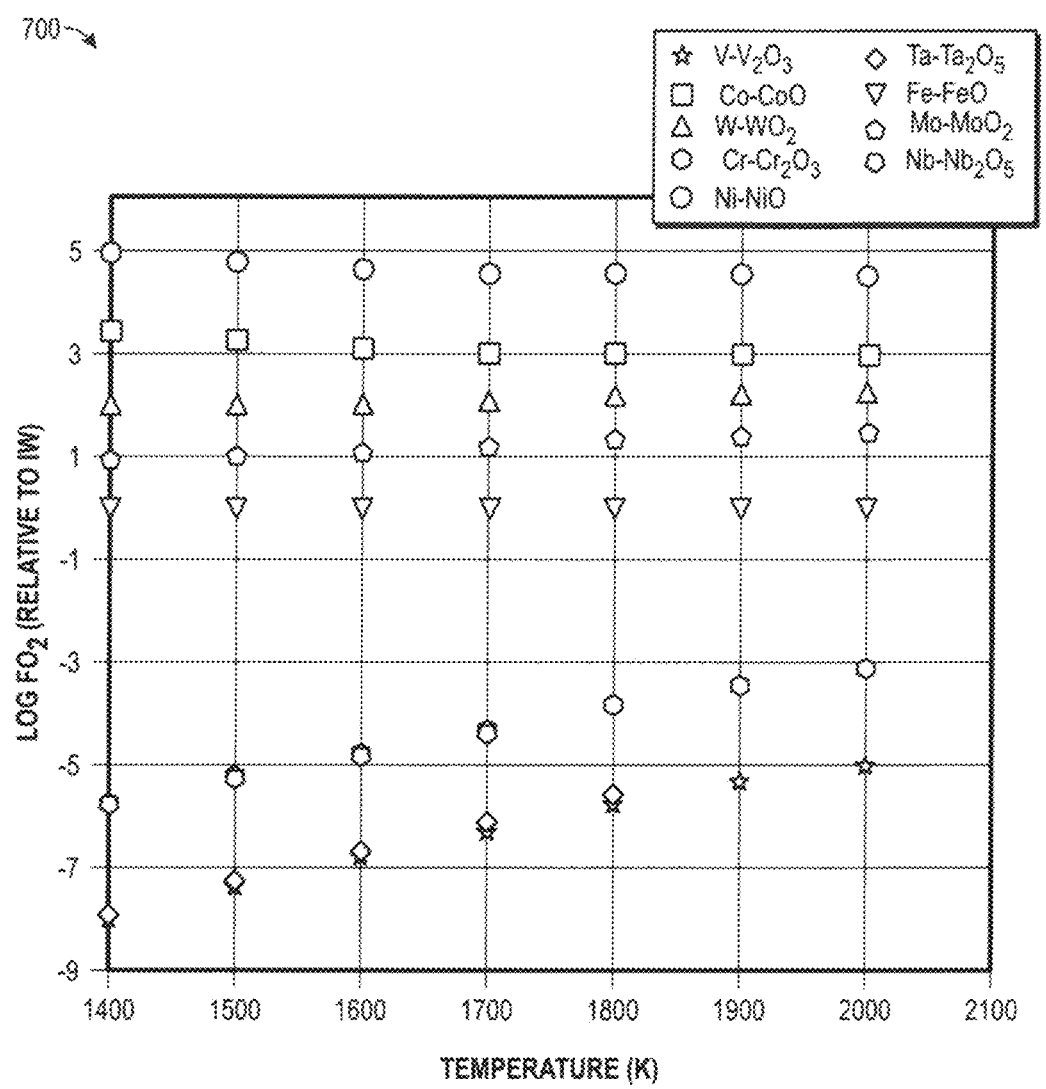
FIG. 7 shows the calculations for oxygen fugacity ($fO_2$) for each of the buffers used, relative to iron-wustite, according to an embodiment. At the temperature of the experiments described herein (1673 K), the range of $fO_2$ covered is from IW+4.5 to IW−6.5, with temperature dependence of most buffers being weak.

The refractory metal-metal oxide pairs listed herein may fix or buffer the oxygen pressure across a range of nearly 12 log $fO_2$ units (see FIG. 7). The approach herein takes the refractory metal-metal oxide pairs to a smaller scale of the high-pressure solid media environment where space is limited.

Examples of the refractory metal-metal-oxide pairs used in experiments for the outer capsule 310 may include—in order of most oxidized to most reduced—Ni—NiO, Co—CoO, Mo—$MoO_2$, W—$WO_2$, Fe—FeO, Cr—$Cr_2O_3$, Nb—$Nb_2O_5$, Ta—$Ta_2O_5$, and V—$V_2O_3$. The oxygen fugacity defined by these metal-metal-oxide pairs may be calculated using thermodynamic data and is shown in FIG. 7. Samples were loaded into a 13 mm non-end-loaded piston-cylinder assembly using $BaCO_3$ as a pressure medium (cell 122), a graphite furnace, and a type C thermocouple to monitor temperature. Samples were pressurized to 1 GPa, heated to 1400° C., and held at this pressure and temperature for 6 hours before power quenching to room temperature.

The outer capsule 310 may at least partially surround or encapsulate the inner capsule 320. The inner capsule 320 may include another material made of, for example, alumina ($Al_2O_3$), graphite, or magnesium oxide (MgO). The inner capsule 320 may at least partially surround or encapsulate a sample 330 to protect/prevent the sample 330 from reacting with the refractory metal and/or the metal oxide. In addition, the inner capsule 320 may be selected as appropriate to minimize reaction with the sample 330.

The sample 330 may be or include solids, liquids, or mixtures of the two. In one embodiment, the sample 330 may include silicate and oxide systems that have higher melting temperatures, such as olivine, pyroxene, spinel, and other oxides. The solid media assembly 100 may be used to test or analyze the sample 330 by using a known equilibrium that is sensitive to $fO_2$ changes to verify the imposed $fO_2$ of the buffer. The solid media assembly 100 may also or instead be used to synthesize the sample 330 at the high temperature and pressure phases at a specified high or low $fO_2$ that would otherwise not be possible in a conventional capsule or assembly. The effect of variable $fO_2$ on phase equilibria or element partitioning can be analyzed.

Figure 4A:
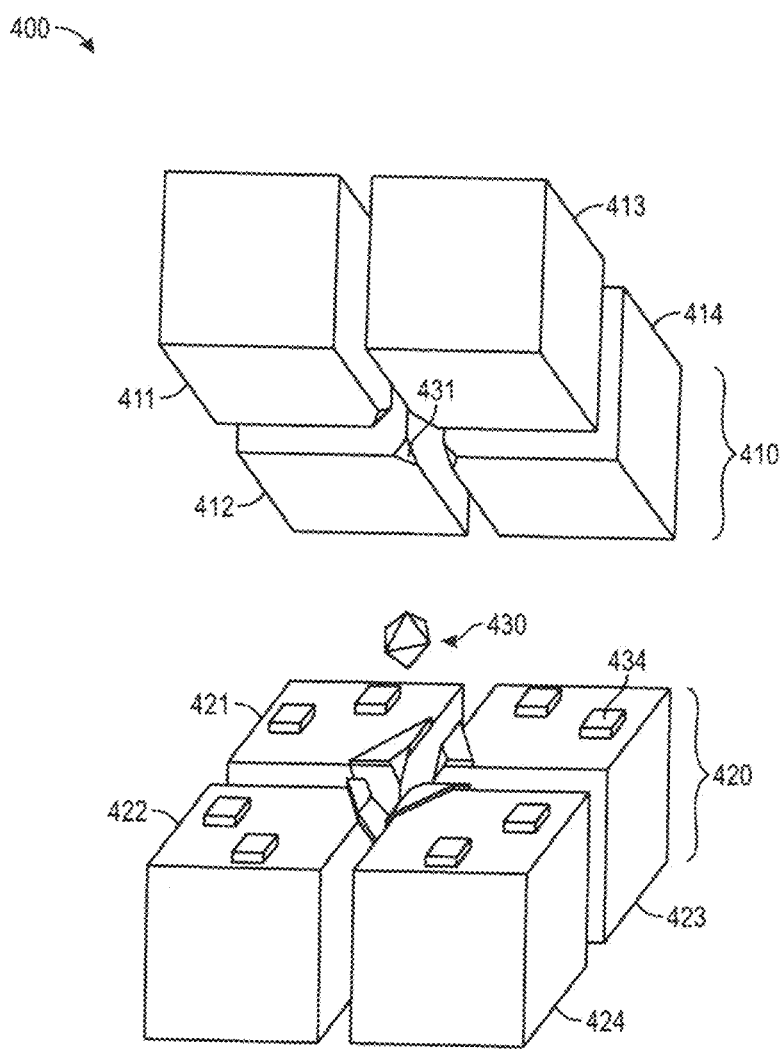
FIG. 4A shows an exploded perspective view of another solid media assembly (e.g., a multi-anvil press assembly) having a pressure assembly and the double capsule assembly positioned therein, according to an embodiment.

FIG. 4A shows a perspective view of another type of solid media assembly (e.g., a multi-anvil assembly) 400 that may control oxygen fugacity, according to an embodiment. The solid media assembly 400 may include one or more (e.g., eight) cubes 411-414, 421-424. The cubes 411-414, 421-424 may be made of, for example, tungsten carbide. An upper layer 410 may include four of the cubes 411-414 arranged in a 2×2 orientation, and a lower layer 420 may include the remaining four of the cubes 421-424 arranged in a corresponding 2×2 orientation.

An inner corner of each of the cubes 411-414, 421-424 may be modified (e.g., machined) to create a planar surface (e.g., a surface of triangular shape) 431 configured to receive a pressure assembly 430. As shown, the pressure assembly 430 may have an octahedral shape configured to match with the modified inner corners (e.g., surfaces 431) of the eight cubes 411-414, 421-424. One or more gaskets 432 and/or spacers 434 may facilitate the receiving of the pressure assembly 430 into the cubes 411-414, 421-424.

Figure 4B:
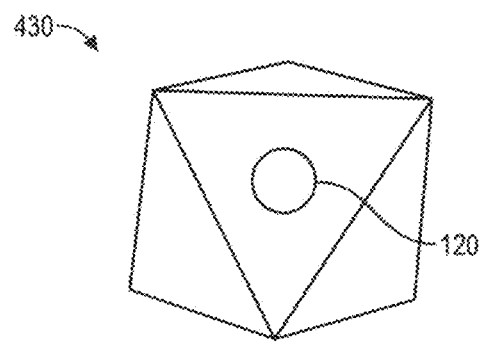
FIG. 4B shows a perspective view of the pressure assembly (from FIG. 4A) having the double capsule assembly positioned therein, according to an embodiment.
Figure 4C:
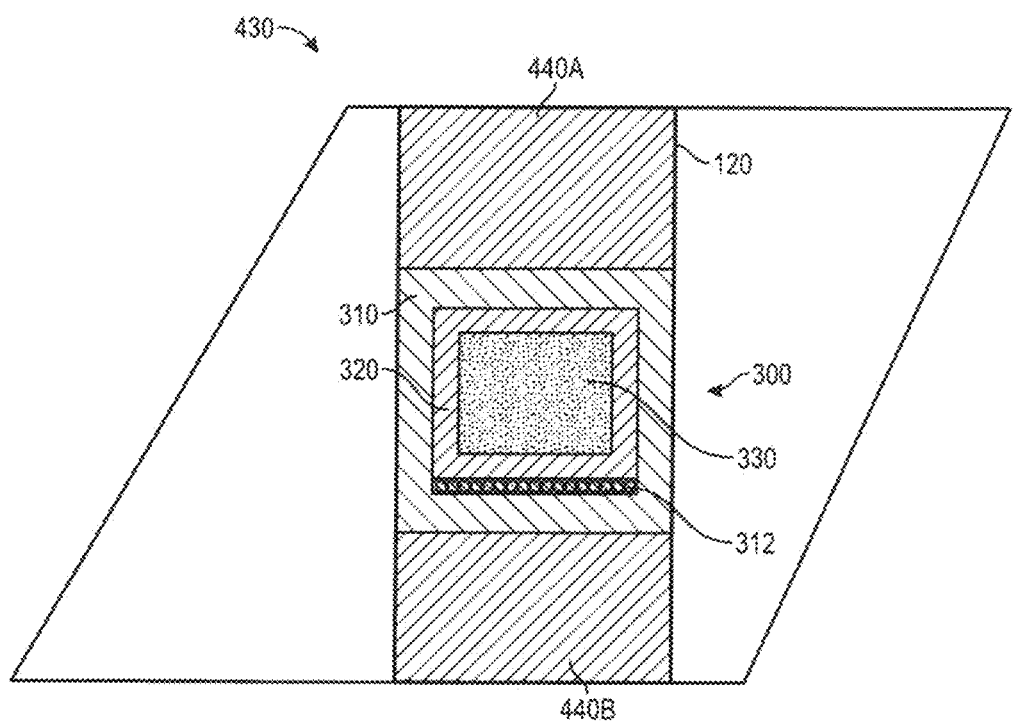
FIG. 4C shows a cross-sectional view of the pressure assembly (from FIG. 4B) having the double capsule assembly positioned therein, according to an embodiment.

As shown in FIGS. 4B and 4C, the furnace 120 and the double capsule assembly 300 may be inserted or positioned within the pressure assembly 430 prior to the pressure assembly 430 being inserted or positioned within the cubes 411-414, 421-424. More particularly, the double capsule assembly 3M) may be inserted or positioned within the furnace 120. As shown, a first (e.g., upper) spacer 440A may be positioned within the furnace 120 and/or above the double capsule assembly 300, and a second (e.g., lower) spacer 440B may be positioned within the furnace 120 and/or below the double capsule assembly 300. The furnace 120 (e.g., including the double capsule assembly 300 and/or the spacers 440A, 440B) may then be inserted or positioned within the pressure assembly 430.

Figure 5:
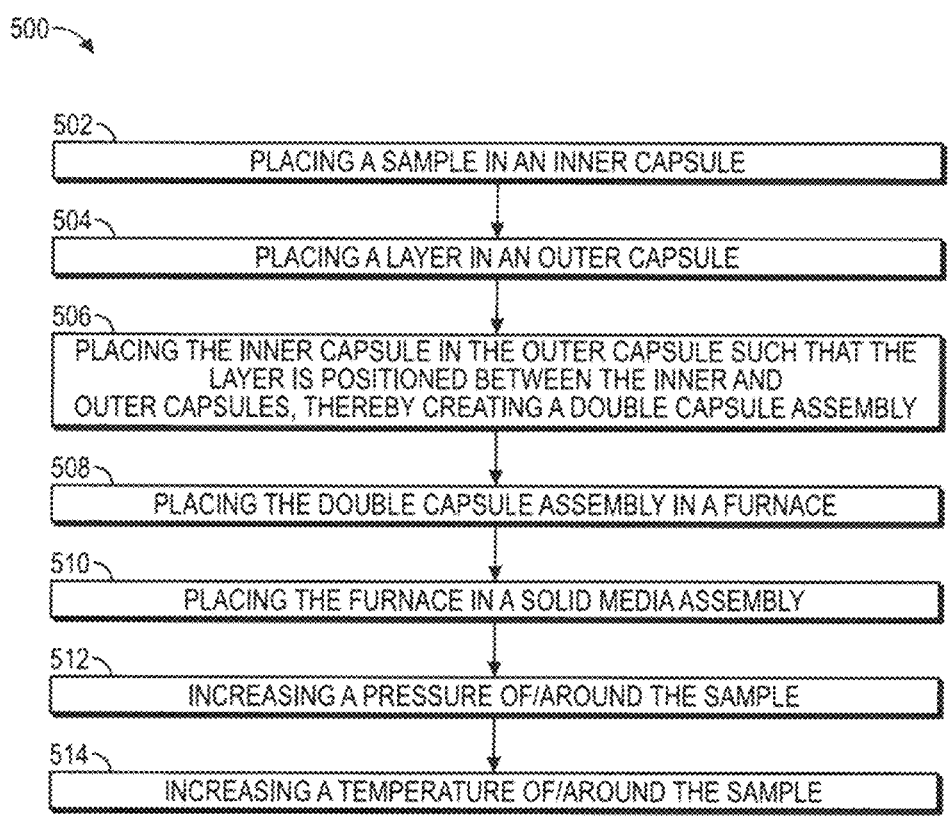
FIG. 5 illustrates a flowchart of a method for analyzing or modifying a sample while controlling oxygen fugacity, according to an embodiment.

FIG. 5 illustrates a flowchart of a method 500 for analyzing or modifying a sample 330 while controlling oxygen fugacity, according to an embodiment. More particularly, the method 500 may be used to test or analyze the sample 330. In another embodiment, the method 500 may be used to synthesize the sample 330.

The method 500 may include placing the sample 330 in the inner capsule 320, as at 502. The method 500 may also include placing the layer 312 in the outer capsule 310, as at 504. The method 500 may also include placing the inner capsule 320 in the outer capsule 310, as at 506. As mentioned above, the layer 312 may be positioned between the outer capsule 310 and the inner capsule 320. The layer 312 may be placed in the outer capsule 310 before, concurrently with, or after the inner capsule 320 is placed in the outer capsule 310. In another embodiment, the layer 312 may be a part of the outer capsule 310. The conclusion of step 504 and/or 506 may yield the double capsule assembly 300.

The method 500 may also include placing the double capsule assembly 300 in the furnace 120, as at 508. The method 500 may also include placing the furnace 120 (with the double capsule assembly 300 therein) in the solid media assembly (e.g., in the piston-cylinder assembly 100 or the multi-anvil press assembly 400), as at 510. In the embodiment of FIGS. 1 and 2, this may include placing the furnace 120 in the cell 122 of the solid media assembly (e.g., piston-cylinder assembly) 100. In the embodiment of FIGS. 4A-4C, this may include placing the furnace 120 in the pressure assembly 430, and subsequently placing the pressure assembly 430 in between the cubes 411-414, 421-424 of the solid media assembly (e.g., multi-anvil press assembly) 400.

The method 500 may also include increasing a pressure of/around the sample 330 while in the solid media assembly 100, 400, as at 512. The pressure may be from about 500 MPa to about 1.5 GPa or about 800 MPa to about 1.2 GPa. The method 500 may also include increasing a temperature of/around the sample 330 while in the solid media assembly 100, 400, as at 514. The temperature may be from about 1000° C. to about 1600° C. or about 1200° C. to about 1500° C.

An oxygen fugacity (e.g., buffer) $fO_2$ may be established by the buffer materials in the double capsule assembly 300 while modifying the pressure and/or temperature. In addition, an oxygen fugacity $fO_2$ may be selected and/or controlled in the double capsule assembly 300 while modifying the pressure and/or temperature. More particularly, the oxygen fugacity $fO_2$ may be selected an/or controlled by selecting the desired $fO_2$ range and appropriate buffer (see FIG. 7).

Analysis of Experiments

The refractory metals and metal oxides were analyzed for major element composition using a JEOL 8530 FEG electron microprobe at NASA Johnson Space Center. A 1-μm beam was used at 20 kV and 10 nA. A variety of natural and synthetic standards were used, including rutile for Ti and O, pure Fe, Ni, Mo, W, Cr metals, and other oxides.

Results of Experiments

Figure 6A:
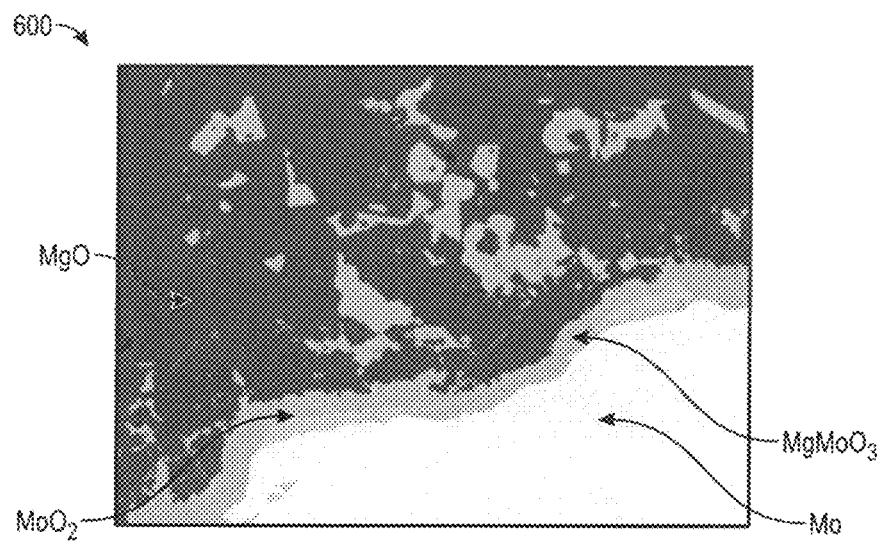
FIGS. 6A, 6B, and 6C show back-scattered electron (BSE) images of experiments using a double capsule assembly, according to an embodiment. More particularly.
Figure 6B:
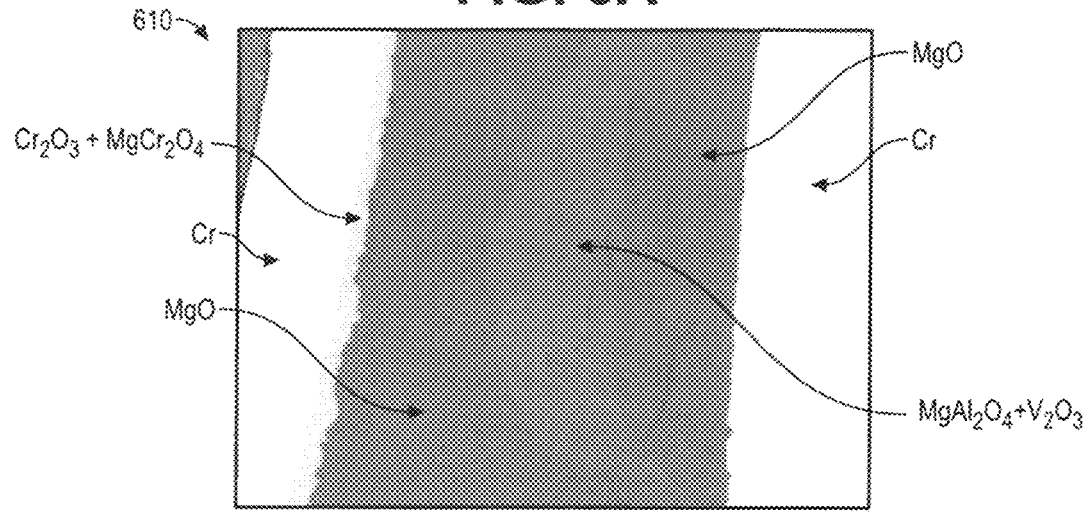
Figure 6C:
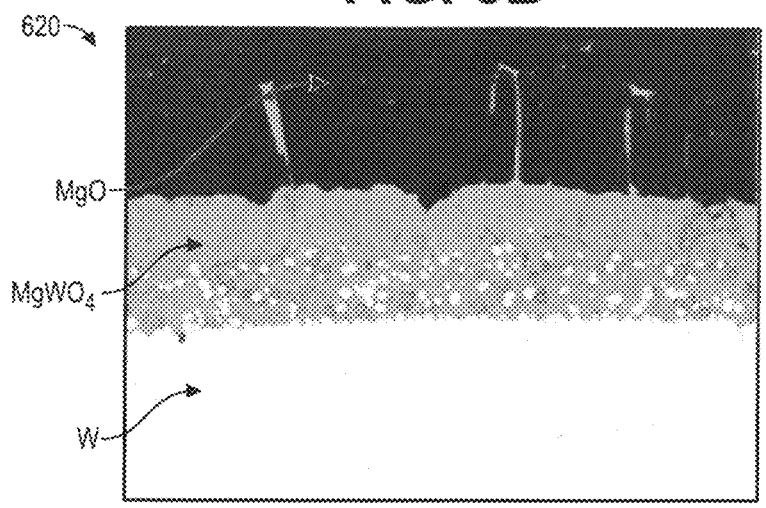

Illustrative textures and results of the experiments using the double capsule assembly (100 or 400) are shown in the backscattered electron (BSE) images in FIGS. 6A-6C. Most experiments exhibited a simple buffer intact such as Ni—NiO, Co—CoO, Mo—$MoO_2$, Fe—FeO, Cr—$Cr_2O_3$, Nb—Nb$_2$O$_5$, Ta—Ta$_2$O$_5$, or V—V$_2$O$_3$ pairs. For example, Mo and MoO$_2$ are shown in FIG. 6A. In addition, MgMoO$_3$ was formed in an experiment shown in the image 600 of FIG. 6A, which does not affect the buffering that is maintained by the Mo and MoO$_2$.

Similarly, the compounds Cr and Cr$_2$O$_3$ are shown in the image 610 of FIG. 6B. The compounds Cr$_2$O$_3$ and MgO react to form MgCr$_2$O$_4$ in the experiment shown in the image 610 of FIG. 63, which does not affect the buffering that is maintained by the Cr and Cr$_2$O$_3$.

In several experiments, the metal reacted with the MgO to form a third phase that can participate in the buffering. For example, as shown in the image 620 of FIG. 6C, MgO and WO$_2$ react to form MgWO$_4$. In this case, because the WO$_2$ is consumed, the buffer becomes W+MgO+O$_2$=MgWO$_4$. The example shown in the image 620 of FIG. 6C also buffers oxygen fugacity, and any such equilibrium can be used in practice as an oxygen buffer as long as thermodynamic data exists for the additional phase. The full range of oxygen fugacity achieved in the experiments is shown in FIG. 7.

Applications

The samples in the inner capsule 320 were MgAl$_2$O$_4$ spinel-doped with a small amount of vanadium (V), with the goal to calibrate the vanadium valence with fO$_2$ for spinels of this composition and then apply the results to natural systems, such as calcium-aluminum-rich inclusions (CAI) systems and other small primitive clasts or particles for which standard redox barometers may be absent. Additional applications are numerous and may include metal-silicate or mineral-melt element partitioning, phase equilibria studies, or mineral or melt syntheses.

In light of the principles and embodiments described and illustrated herein, it will be recognized that the embodiments can be modified in arrangement and detail without departing from such principles. Also, the foregoing discussion has focused on particular embodiments, but other configurations are contemplated. In particular, even though expressions such as "in an embodiment," "in another embodiment," "in a version of the embodiment" or the like are used herein, these phrases are meant to generally reference the range of possibilities of embodiments, and are not intended to limit the disclosure to the particular embodiments and configurations described herein. As used herein, these terms may reference the same or different embodiments that are combinable into other embodiments.

Similarly, although examples of processes have been described with regard to particular operations performed in a particular sequence, numerous modifications could be applied to those processes to derive numerous alternative embodiments of the content described herein. For example, alternative embodiments may include processes that use fewer than all of the disclosed operations, processes that use additional operations, and processes in which the individual operations disclosed herein are combined, subdivided, rearranged, differently ordered or otherwise altered.

In view of the wide variety of useful permutations that may be readily derived from the exemplary embodiments described herein, this detailed description is intended to be illustrative only, and should not be taken as limiting the scope of the disclosure.

What is claimed is:

1. A solid media assembly, comprising:
    a furnace; and
    a double capsule assembly positioned within the furnace, wherein the double capsule assembly comprises:
        an outer capsule;
        an inner capsule configured to be positioned within the outer capsule, wherein the inner capsule is configured to have a sample positioned therein; and
        a layer positioned between the outer capsule and the inner capsule,
    wherein a first material of the outer capsule, a second material of the inner capsule, a third material of the layer, or a combination thereof are selected to form an oxygen buffer for control of oxygen fugacity in the double capsule assembly during a test of the sample, wherein the first material of the outer capsule comprises a metal, and wherein the third material of the layer comprises the metal in a metal-oxide powder form.

2. The solid media assembly of claim 1, wherein the metal is selected from the group consisting of iron, nickel, cobalt, molybdenum, tungsten, vanadium, chromium, and niobium, and wherein the layer is selected from the group consisting of iron oxide, nickel oxide, cobalt oxide, molybdenum oxide, tungsten oxide, vanadium oxide, chromium oxide, and niobium oxide.

3. The solid media assembly of claim 1, wherein the inner capsule is made from a different material than the metal of the outer capsule.

4. The solid media assembly of claim 3, wherein the inner capsule is made from graphite, alumina, or magnesium oxide.

5. The solid media assembly of claim 3, wherein the inner capsule prevents the sample from reacting with the outer capsule and the layer.

6. The solid media assembly of claim 1, wherein the solid media assembly comprises a piston-cylinder assembly.

7. The solid media assembly of claim 1, wherein the solid media assembly comprises a multi-anvil press assembly.

8. The solid media assembly of claim 7, further comprising an octahedral pressure assembly configured to have the furnace positioned therein.

9. An apparatus for controlling oxygen fugacity in a solid media assembly when performing a test on a sample comprising:
    a double capsule assembly configured to be positioned within a furnace of the solid media assembly, wherein the double capsule assembly comprises:
        an outer capsule made of a first metal and having an inner surface;
        an inner capsule having an outer surface and positioned within the outer capsule, the inner capsule configured to have a sample positioned therein; and
        a layer made of a metal-oxide positioned in a location within the outer capsule and outside the inner capsule, wherein the layer is positioned between the inner surface of the outer capsule and the outer surface of the inner capsule, wherein the metal-oxide of the layer comprises a metal oxide of metal that is the same as the first metal and in a powder form.

10. The apparatus of claim 9, wherein an oxygen buffer is formed and at least partially surrounds the inner capsule during the test.

11. The apparatus of claim 9, wherein the layer has a thickness from about 100 μm to about 200 μm.

12. The apparatus of claim 9 wherein the combination of first metal and metal-oxide powder to construct the double capsule assembly is selected from the group comprising Ni—NiO, Co—CoO, Mo—MoO2, Fe—FeO, W—WO2, Cr—Cr2O3, V—V2O3, and Nb—Nb2O5.

* * * * *